United States Patent
Napoletano et al.

(10) Patent No.: US 7,081,534 B2
(45) Date of Patent: *Jul. 25, 2006

(54) PROCESS FOR THE PREPARATION OF PANTOPRAZOLE AND SALTS THEREOF

(75) Inventors: Caterina Napoletano, Laveno Mombello (IT); Eleonora Porta, Erba (IT); Pietro Allegrini, San Donato Milanese (IT); Graziano Castaldi, Briona (IT)

(73) Assignee: Dipharma S.p.A., Mereto di Tomba (IT)

(*) Notice: Subject to any disclaimer, the term of this patent is extended or adjusted under 35 U.S.C. 154(b) by 0 days.

This patent is subject to a terminal disclaimer.

(21) Appl. No.: 10/946,112

(22) Filed: Sep. 22, 2004

(65) Prior Publication Data

US 2005/0096352 A1   May 5, 2005

(30) Foreign Application Priority Data

Sep. 23, 2003   (IT) .......................... MI2003A1813

(51) Int. Cl.
*C07D 401/12* (2006.01)
(52) U.S. Cl. .................................... 546/273.7
(58) Field of Classification Search ............. 546/273.7
See application file for complete search history.

(56) References Cited

U.S. PATENT DOCUMENTS 6,124,464 A * 9/2000 Hogberg et al. ......... 546/273.7
6,723,852 B1 * 4/2004 Berenguer Maimo .... 546/273.4

FOREIGN PATENT DOCUMENTS

EP    1 466 897    10/2004
WO   WO 02/28852   4/2002

OTHER PUBLICATIONS

Modi et al., "A process for the manufacture, etc.," CA 140: 270848 (1997).*
Mathad et al., "An Improved and single, etc.", Organic Process Research & Development, 2004, 8, 266-270.*

* cited by examiner

*Primary Examiner*—Patricia L. Morris
(74) *Attorney, Agent, or Firm*—Young & Thompson

(57) ABSTRACT

A process for the preparation of pantoprazole and the salts thereof, comprising the reaction of a mercaptoimidazole with a picoline, to give a 2-pyridinyl-methylsulfinyl-2-benzimidazole intermediate, the oxidation thereof with ε-phthalimidoperhexanoic acid and the subsequent methoxylation.

18 Claims, No Drawings

PROCESS FOR THE PREPARATION OF PANTOPRAZOLE AND SALTS THEREOF

FIELD OF THE INVENTION

The present invention relates to a novel process for the preparation of pantoprazole, namely 5-(difluoromethoxy)-2-[[3,4-dimethoxy-2-pyridinyl)methyl]sulfinyl]-1H-benzimidazole, and pharmaceutically acceptable salts thereof.

PRIOR ART

Pantoprazole, an inhibitor of acid gastric secretion used in therapy for the treatment of gastric ulcer, is disclosed in EP 166287. Pantoprazole belongs to the so-called class of anti-ulcer prazols. The main steps for the preparation of said compounds are the reaction between a mercaptoimidazole intermediate with a picoline intermediate and the oxidation of the resulting thioether compound (—S—), to give the corresponding sulfinyl compound (—SO—). In particular, U.S. Pat. No. 5,391,752, for example, teaches to carry out said oxidation with magnesium monoperoxyphthalate. U.S. Pat. No. 6,303,787 cites, among the possible oxidizers, metachloroperbenzoic acid, hydrogen peroxide in the presence of a catalyst, such as ammonium molybdate and vanadium pentoxide and urea-hydrogen peroxide complexes. U.S. Pat. No. 5,948,789 teaches the use of hydroperoxides, such as tert-butylhydroperoxide and cumene hydroperoxide.

The processes to date described for the preparation of pantoprazole suffer anyway of some drawbacks and there is still the need for a safer, less costly and more efficient synthetic procedure, which at the same time provides pantoprazole in a sufficiently pure form to meet regulatory requirements while producing by-products which are easily removed with low costs, without damaging the environment.

The object of the present invention is to provide a novel, more advantageous alternative process for the preparation of pantoprazole, which affords this product in highly pure form, through a synthetic route which is simple, economic and easy-to-carry out.

DETAILED DISCLOSURE OF THE INVENTION

The present invention relates to a process for the preparation of pantoprazole of formula (I),

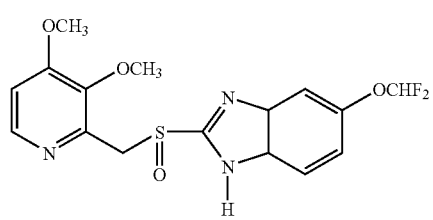

and the pharmaceutically acceptable salts thereof, which process comprises:

a) the reaction between a compound of formula (II), or a salt thereof,

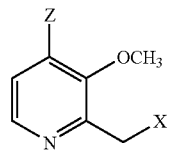

wherein each of X and Z, which can be the same or different, is a leaving group, with a compound of formula (III)

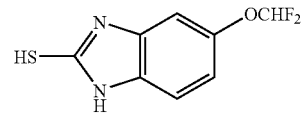

to obtain a thioether compound of formula (IV);

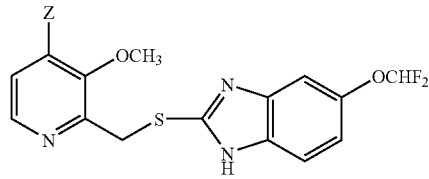

wherein Z is as defined above;

b) the oxidation of a compound of formula (IV) with ε-phthalimidoperhexanoic acid, to obtain a sulfinyl compound of formula (V),

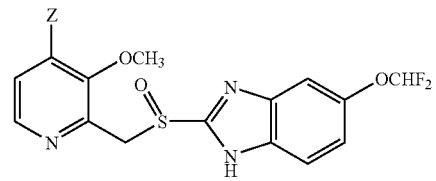

wherein Z is as defined above; and c) the methoxylation of a compound (V), to obtain a compound of formula (I);

and the optional salification to obtain a pharmaceutically acceptable salt thereof.

Preferred pantoprazole salts obtainable by the process of the invention are the salts with the inorganic or organic bases used in pharmaceutical technique, such as the sodium, potassium, calcium, magnesium and aluminium salts, both anhydrous and hydrates, particularly the hydrate sodium salt, preferably the sesquihydrate.

A salt of a compound of formula (II) is, for example, a salt with hydrochloric, hydrobromic, acetic, nitric, sulfuric or phosphoric acid, preferably hydrochloric acid.

The leaving group Z or X is for example a halogen atom, in particular chlorine, or a hydroxyl group activated by esterification, for example through an alkanesulfonate group, typically the mesylate, or an arylsulfonate group, typically the tosylate, or a perfluoroalkanesulfonate group, for example trifluoromethanesulfonate and nonafluorobutanesulfonate.

The compounds of formula (II) and (III) are either known, for example by WO 02/28852, or can be obtained with known methods.

The reaction between a compound of formula (II), or a salt thereof, and a compound of formula (III) is carried out in an organic solvent or in mixtures of organic solvents. Examples of said solvents are aliphatic chlorides, in particular methylene chloride, chloroform, carbon tetrachloride, trichloroethane, tetrachloroethylene, preferably methylene chloride; aromatic chlorides, in particular chlorobenzene and ortho-dichloro-benzene, the latter being preferred; aliphatic and aromatic hydrocarbons, in particular pentane, hexane, cyclohexane, benzene, ortho-, meta- and para-xylene and toluene, the latter being preferred, or mixtures thereof with $C_1$–$C_4$ alkanols, preferably mixtures of toluene and methanol; carboxylic acid esters, in particular methyl, ethyl, propyl, isopropyl, butyl and isobutyl acetates, preferably ethyl acetate; alkyl carbonates, such as dimethyl carbonate; alkyl and cycloalkyl ketones, for example acetone, methyl-ethyl-ketone, methyl isobutyl ketone and cyclohexanone. Particularly preferred are aliphatic and aromatic hydrocarbon solvents, such as pentane, hexane, cyclohexane, benzene and toluene, or mixtures thereof with $C_1$–$C_4$ alkanols, preferably mixtures of toluene and methanol. The reaction is preferably carried out in the presence of a basic agent, for example an alkali metal alcoxide or hydroxide, such as sodium or potassium, in particular sodium methoxide. The amount of basic agent depends on whether the compound of formula (II) is used in the free or salified form. The compound of formula (II) is preferably used in the salified form and the amount of basic agent ranges approx. from 2.0 to 2.5 mols per mole of compound of formula (III), preferably about 2.0. The reaction temperature ranges from about 0° C. to the reflux temperature of the solvent, preferably approx. from 15 to 40° C.

The oxidation of the thioether compound of formula (IV) is carried out by addition of ε-phthalimidoperhexanoic acid, optionally dispersed in an organic solvent, to the reaction mixture. The amount of ε-phthalimidoperhexanoic acid typically ranges from approx. 0.8 to 1.5 equivalents, preferably from 0.9 to 1.1 equivalents, per equivalent of thioether compound of formula (IV). The reaction time usually ranges from about 0.5 hours to about 3 hours, preferably from about 1 hour to about 2 hours. The reaction temperature ranges approx. between −20° C. and the reflux temperature of the solvent, in particular between 0 and 40° C.

The organic solvent in which ε-phthalimidoperhexanoic acid is dispersed can be an organic solvent, either water-miscible or water-immiscible. Examples of said solvent are aliphatic chlorides, in particular methylene chloride, chloroform, carbon tetrachloride, trichloroethane, tetrachloroethylene, preferably methylene chloride; aromatic chlorides, in particular chlorobenzene and ortho-dichlorobenzene, the latter being preferred; aromatic hydrocarbons, in particular benzene, ortho-, meta- and para-xylene and toluene, the latter being preferred; carboxylic acid esters, in particular methyl, ethyl, propyl, isopropyl, butyl and isobutyl acetates, preferably ethyl acetate; and alkyl carbonates, such as dimethyl carbonate; $C_1$–$C_5$ alkanols, such as methanol, ethanol, propanol, iso-propanol, n-butanol, sec-butanol and tert-butanol, in particular iso-propanol; alkyl and cycloalkyl ketones, for example acetone, methyl ethyl ketone, methyl isobutyl ketone and cyclohexanone. Particularly preferred solvents are aliphatic or aromatic hydrocarbons, such as pentane, hexane, cyclohexane, benzene, toluene, or mixtures thereof, particularly toluene.

The methoxylation of the sulfinyl compound of formula (V) is performed in the presence of an alkali metal methoxide, for example sodium or potassium methoxide, in an organic solvent, typically methanol. The concentration of methoxide in said solution is approx. 20–40%, preferably 30%. The reaction is carried out at a temperature preferably ranging from room temperature to the reflux temperature of the reaction mixture.

The resulting compound of formula (I) is extracted in an alkali aqueous phase and precipitated by adjusting the pH of the solution to about 9, at room temperature, thereby recovering pantoprazole, which is subsequently washed. Alternatively, the pantoprazole salt present in the aqueous solution is extracted with a suitable organic solvent, for example a ketone, in particular methyl ethyl ketone, methyl isobutyl ketone or cyclohexanone, preferably methyl isobutyl ketone. The salt of pantoprazole can then be crystallized from the extraction solvent itself or from a suitable organic solvent as known in the art. If necessary, pantoprazole can be subjected to further purifications, according to known methods, for example by crystallization from one or more organic solvents.

The optional conversion of pantoprazole into a pharmaceutically acceptable salt thereof can be carried out according to known methods.

The process for the preparation of pantoprazole, according to the invention, has a number of advantages compared with the known ones. For example, at least two of the three main synthetic steps can be carried out in the same reactor and in the same solvent, with no need to isolate and purify the intermediate of formula (IV). This makes the synthesis faster, therefore reducing production costs.

According to a preferred aspect of the invention, steps a) and b) of the process are carried out in the same solvent, preferably toluene or mixtures thereof with methanol, and in the same reactor.

ε-Phthalimidoperhexanoic acid is a commercially available product, which is stable, solid, inexpensive, used for the preparation of cosmetic formulations and both household and industrial detergents. ε-Phthalimidoperhexanoic acid, used as the reagent in the oxidation of the thioether intermediate of formula (IV), is easy and safe to handle, and its use on an industrial scale requires neither specific plants, nor safety devices and procedures. Moreover, ε-phthalimidoperhexanoic acid and its reduction product, ε-phthalimidohexanoic acid, are low-polluting and therefore can be advantageously used on a large scale. Furthermore, it has been found that the use of ε-phthalimidoperhexanoic acid as oxidizing agent, according to the invention, allows to predict and control the kinetics of the oxidation reaction thereby avoiding formation of by-products with different oxidation degree, such as N-oxides and/or sulfonyl (—SO2-) derivatives and/or dangerous accumulations of oxidizer. Conversely, said accumulations take place with other known oxidizing agents, for example with peracetic acid/hydrogen peroxide/acetic acid aqueous solution, which contains about 15% of active oxygen. Therefore, the oxidation reaction can be easily carried out on a large scale without particular hazards. Moreover, the chemical-physical properties of the reduced by-product, ε-phthalimidohexanoic acid, allow to easily recover the resulting pantoprazole, in highly pure form, without the need for cumbersome and costly purification processes. In fact, ε-phthalimidohexanoic acid is soluble in alkali aqueous solution, where the basic agent is selected from e.g. an alkali or alkaline-earth hydroxide, typically sodium or potassium hydroxide, ammonium hydroxide or monomethylamine. Therefore, when the oxidation reaction is carried out in an apolar aprotic organic solvent, as mentioned above, which is water-immiscible, ε-phthalimidohexanoic acid can be removed from the reaction mixture simply by washing with an alkali aqueous solution.

The following examples illustrate the invention.

EXAMPLE 1

Synthesis of 2-chloromethyl-3-methoxy-4-chloro-pyridine (II)

A 1000 ml round-bottom flask is loaded with 67 g (0.319 mol) of 2-hydroxymethyl-3-methoxy-4-chloro-pyridine hydrochloride and 469 ml of toluene. 73 g (0.606 mol) of thionyl chloride are then dropped therein, under stirring and at inner temperature of about 15–25° C. After completion of the addition, the mixture is washed with 35 ml of toluene, keeping the suspension at this temperature for at least 1 hour. After completion of the reaction, approx. 200 ml of solvent are distilled off under vacuum. The suspension, containing 2-chloromethyl-3-methoxy-4-chloro-pyridine, is then subjected to the subsequent step.

EXAMPLE 2

Synthesis of (5-difluoromethoxy)-2-[(4-chloro-3-methoxy-2-pyridinyl)methyl]thio-1H-benzimidazole (IV)

The suspension, containing 2-chloromethyl-3-methoxy-4-chloro-pyridine, obtained according to the procedure of example 1, is diluted at about 15–25° C. with 219 ml of methanol until complete dissolution. 58 g (0.319 mol) of NaOCH$_3$ (30% w/w solution) are dropped into the solution, keeping the inner temperature below 25° C., finally washing with 10 ml of methanol. The mixture is kept at approx. 15–25° C. for 1 hour, then 76 g (0.351 mol) of 5-difluoromethoxy-2-mercapto-benzimidazole are added, stirring for 30 minutes. 63 g (0.351 mol) of NaOCH$_3$ (30% w/w solution) are then added dropwise, keeping the inner temperature at approx. 20–35° C. After completion of the addition the mixture is washed with 10 ml of methanol. The resulting suspension is kept for about 1 hour at about 15–25° C. After completion of the reaction, a solution of 197 ml of water and 19 ml (0.191 mol) of 30% NaOH is added dropwise, thereby obtaining a suspension which is kept under stirring for approx. 30 minutes and concentrated by distillation of 410 ml of solvent, reaching 87° C. inner temperature. Thereafter, 131 ml of water are added dropwise, followed by 119 ml of toluene at a temperature below 80° C. The mixture is refluxed for 30 minutes to obtain a solution from which the product crystallizes upon slow cooling. Alternatively, the organic phase is separated and subjected to the subsequent step. When carrying out the crystallization of intermediate (IV), this is recovered by filtration, after cooling at about 15–25° for 1 hour, and washed twice on the filter first with 120 ml of toluene, then with water, until neutral pH and absence of chlorides. 155 g of wet product are obtained, which is dried under vacuum to obtain 98.1 g of dry product (yield=82.8%).

EXAMPLE 3

Synthesis of 5-(difluoromethoxy)-2-[[(4-chloro-3-methoxy-2-pyridinyl)methyl]sulfinyl]-1H-benzimidazole (V)

50 g of (5-difluoromethoxy)-2-[(4-chloro-3-methoxy-2-pyridinyl)methyl]thio-1H-benzimidazole and 150 ml of isopropyl alcohol are placed in a 1000 ml round-bottom flask. A solution of ε-phthalimidoperhexanoic acid (70% w/w; 50.64 g.) in isopropyl alcohol (150 ml), kept at about 40° C., is dropped in the suspension kept at 20° C.±5° C., in 45 to 90 minutes. After completion of the addition, the mixture is left to spontaneously cool to room temperature, keeping these conditions for about 5 hours. Afterwards, 225 ml of water are added and the mixture is stirred for 24 to 48 hours at room temperature, then filtered at approx. 20±5° C., washing with a 1/1 v/v isopropanol/water mixture. The reaction mixture is then dried in a ventilated dryer at room temperature, to obtain 44 g of (5-difluoromethoxy)-2-[(4-chloro-3-methoxy-2-pyridinyl)methyl]sulfinyl-1H-benzimidazole, as a white solid (molar yield on the sulfide=84.4%).

EXAMPLE 4

Synthesis of 5-(difluoromethoxy)-2-[[(4-chloro-3-methoxy-2-pyridinyl)methyl]sulfinyl]-1H-benzimidazole (V), without isolating the intermediate of formula (IV)

The toluene solution prepared as described in Example 2 is diluted with about 1000 ml of toluene and heated to approx. 55° C. A solution of ε-phthalimidoperhexanoic acid (70% w/w; 122 g) in toluene (1150 ml) is then added in one hour. After completion of the reaction, the solvent is evaporated off by distillation under vacuum and the hot residue is taken up with isopropanol (700 ml) and water (520 ml). The mixture is cooled to room temperature and left under stirring for 24 to 48 hours, then filtered at approx. 20±5° C., washing with a 1/1 v/v isopropanol/water mixture. The reaction mixture is then dried in a ventilated static dryer at room temperature, to obtain 95 g of (5-difluoromethoxy)-2-[(4-chloro-3-methoxy-2-pyridinyl)methyl]sulfinyl-1H-benzimidazole, as a white solid.

EXAMPLE 5

Synthesis of 5-(difluoromethoxy)-2-[[(3,4-of-methoxy-2-pyridinyl)methyl]sulfinyl]-1H-benzimidazole sodium salt, sesquihydrate (I)

A 3000 ml round-bottom flask is loaded with 464 g (2.58 mol) of a 30% solution of sodium methoxide in methanol and heated at 50° C. 200 g (0.516 mol) of 5-(difluoromethoxy)-2-[[(4-chloro-3-methoxy-2-pyridinyl)methyl] sulfinyl]-1H-benzimidazole are then added in portions, while refluxing to complete the reaction. The reaction mixture is cooled to 35° C. and added with 700 ml of demineralised H$_2$O and 2000 ml of toluene, in portions. All the methanol is removed by azeotropical distillation under reduced pressure (about 50 mm Hg) without exceeding 35° C. Demineralised H$_2$O is then added at 50° C. until complete dissolution and the pantoprazole sodium salt is extracted by adding 850 ml of methyl ethyl ketone, then separating the exhausted aqueous phase. The organic phase is partially concentrated and cooled to 20° C.; the crystallized product is filtered and washed with 200 ml of methyl ethyl ketone and 200 ml of acetone. 185 g of wet product are obtained (equivalent to 148 g dry product-yield=70.8%). The resulting pantoprazole sodium sesquihydrate can be further purified according to known methods.

What is claimed is:

1. A process for the preparation of pantoprazole of formula (I),

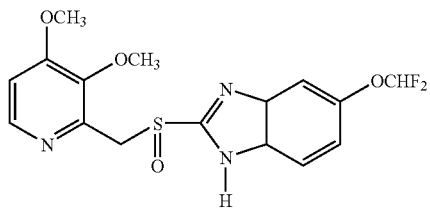

or a pharmaceutically acceptable salt thereof, which process comprises:

a) a reaction between a compound of formula (II), or a salt thereof,

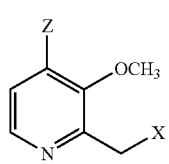

wherein each of X and Z, which can be the same or different, is a leaving group, with a compound of formula (III)

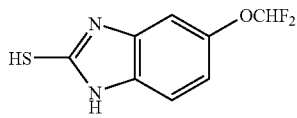

to obtain a thioether compound of formula (IV);

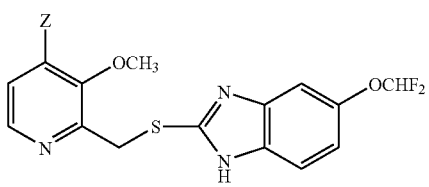

b) an oxidation of a compound of formula (IV) with ε-phthalimidoperhexanoic acid, to obtain a sulfinyl compound of formula (V),

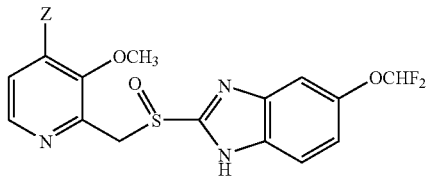

wherein Z is as defined above; and c) the methoxylation of a compound (V), to obtain a compound of formula (I);

and its optional salification to obtain a pharmaceutically acceptable salt thereof.

2. The process according to claim 1, wherein step a) is carried out in a aliphatic or aromatic hydrocarbon solvent, or mixtures thereof with $C_1$–$C_4$ alkanols.

3. The process according to claim 1, wherein in step a) a compound of formula (II) is reacted in salified form and the reaction is carried out in the presence of a basic agent.

4. The process according to claim 3, wherein the amount of basic agent ranges from 2.0 to 2.5 mols per mole of compound of formula (III).

5. The process according to claim 1, wherein in step b) the amount of ε-phthalimidoperhexanoic acid ranges from 0.8 to 1.5 equivalents per equivalent of thioether compound of formula (IV).

6. The process according to claim 5, wherein the oxidation is carried out in an aliphatic or aromatic hydrocarbon solvent.

7. The process according to claim 1, wherein steps a) and b) are carried out in the same solvent.

8. The process according to claim 7, wherein the solvent is toluene or mixtures thereof with methanol.

9. The process according to claim 1, wherein in step b) the oxidation of a compound of formula (IV) is performed at a temperature approximately between −20° C. and the reflux temperature of the solvent, in a water-miscible or water-immiscible organic solvent.

10. The process according to claim 9, wherein step a) is carried out in an aliphatic or aromatic hydrocarbon solvent, or mixtures thereof with $C_1$–$C_4$ alkands, and wherein in step b) the oxidation of a compound of formula (IV) is performed at a temperature approximately between −20° C. and the reflux temperature of the solvent, in a water-miscible or water-immiscible organic solvent.

11. The process according to claim 9, wherein in step a) a compound of formula (II) is reacted in a salified form and the reaction is carried out in the presence of a basic agent.

12. The process according to claim 11, wherein the amount of basic agent ranges from 2.0 to 2.5 mols per mole of compound of formula (III).

13. The process according to claim 9, wherein in step b) the amount of ε-phthalimidoperhexanoic acid ranges from 0.8 to 1.5 equivalents per equivalent of thioether compound of formula (IV).

14. The process according to claim 10, wherein in step b) the amount of ε-phthalimidoperhexanoic acid ranges from 0.8 to 1.5 equivalents per equivalent of thioether compound of formula (IV).

15. The process according to claim 9, wherein steps a) and b) are carried out in the same solvent.

16. The process according to claim 10, wherein steps a) and b) are carried out in the same solvent.

17. The process according to claim 9, wherein the oxidation is carried out in an aliphatic or aromatic hydrocarbon solvent.

18. The process according to claim 10, wherein the oxidation is carried out in an aliphatic or aromatic hydrocarbon solvent.

* * * * *